United States Patent
Gagnieux et al.

(10) Patent No.: US 8,939,288 B2
(45) Date of Patent: Jan. 27, 2015

(54) PACKAGING FOR CYLINDRICAL CONTAINERS

(75) Inventors: Samuel Gagnieux, Saint-Martin-le-Vinoux (FR); Thomas Dubois, Echirolles (FR)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 26 days.

(21) Appl. No.: 13/823,417

(22) PCT Filed: Sep. 28, 2010

(86) PCT No.: PCT/IB2010/002765
§ 371 (c)(1),
(2), (4) Date: Mar. 14, 2013

(87) PCT Pub. No.: WO2012/042291
PCT Pub. Date: Apr. 5, 2012

(65) Prior Publication Data
US 2013/0186793 A1    Jul. 25, 2013

(51) Int. Cl.
B65D 85/20    (2006.01)
A61B 19/02    (2006.01)
A61M 5/00    (2006.01)
B65D 25/10    (2006.01)

(52) U.S. Cl.
CPC .............. A61M 5/002 (2013.01); B65D 25/108 (2013.01); *A61M 5/008* (2013.01)
USPC .............. 206/366; 206/439; 206/443; 442/28

(58) Field of Classification Search
USPC ................. 206/366, 370, 438, 439, 558, 443; 422/22–28; 211/74
See application file for complete search history.

(56) References Cited

U.S. PATENT DOCUMENTS

| 5,121,832 | A  | * | 6/1992  | Fiocchi .......................... 206/558 |
| 6,098,802 | A  | * | 8/2000  | Asa et al. ...................... 206/443 |
| 6,164,044 | A  | * | 12/2000 | Porfano et al. .................. 422/28 |
| 7,100,768 | B2 | * | 9/2006  | Grimard et al. ............... 206/439 |
| 7,303,073 | B2 | * | 12/2007 | Raynal-Olive et al. ........ 206/439 |
| 7,431,157 | B2 | * | 10/2008 | Porret et al. ................... 206/439 |
| 8,056,719 | B2 | * | 11/2011 | Porret et al. ................... 206/439 |
| 8,490,790 | B2 | * | 7/2013  | Cocheteux et al. ........... 206/366 |
| 2012/0118777 | A1 | * | 5/2012 | Kakiuchi et al. .............. 206/366 |

FOREIGN PATENT DOCUMENTS

| EP | 1449551 A1 | 8/2004 |
| WO | 0240064 A1 | 5/2002 |
| WO | 03089028 A1 | 10/2003 |
| WO | 2011015896 A1 | 2/2011 |

* cited by examiner

*Primary Examiner* — Bryon Gehman
(74) *Attorney, Agent, or Firm* — The Webb Law Firm

(57) ABSTRACT

A packaging including a grouping nest for receiving syringes, a packaging tub, and a sealing cover for sealing the packaging tub. The packaging includes a plate intended to be positioned close to the flanges of the syringes before sealing of the tub; this plate includes a plurality of first surfaces intended to be placed in contact with the flanges and a plurality of second surfaces located on the side of the cover plate opposite this plurality of first surfaces, the distance between the plurality of first surfaces and the plurality of second surfaces being chosen in such a way that, when the plurality of first surfaces lies against the flanges, the plurality of second surfaces is in contact or in close proximity to the sealing cover.

12 Claims, 3 Drawing Sheets

PACKAGING FOR CYLINDRICAL CONTAINERS

This invention is directed to a packaging for a cylindrical container such as, for example, a syringe, cartridge, or other cylindrical container having a flange. Each cylindrical container comprises a cylindrical body, in particular tubular, and a flange located at or near an end of the body. The flange can be unitarily formed with the syringe body or can be a separate piece mounted on or to the body.

Often the syringes must be transported from one site to another, when they are manufactured in one site and filled in another site, or, less frequently, when they are manufactured and filled in the same site and must be delivered, once filled, in another site.

For this transport, the syringes are usually put in a package comprising (i) a grouping tray or nest, (ii) a packaging tub, and (iii) a sealing cover. The tray or nest comprises openings coaxially surrounded by chimneys for receiving syringes having their flanges abutting against the upper ends of the chimneys. The tray or nest is placed in the packaging tub, which is then sealed by the sealing cover and sterilised. When received at the destination, the tub is opened by automated means and the tray or nest is extracted therefrom, and then can be used for the handling and/or for filling the syringes.

The inner surface of the syringe bodies is generally coated to improve the subsequent sliding of the syringe pistons or stoppers against the syringe bodies, the coating being a silicon-type lubricant, for example. Due to the presence of such coating on the inner surface of the syringe bodies, the tub containing the syringes needs to be transported upside down to avoid any drop of the coating to fall into the tip and/or the injection needle of the syringes and to block these openings.

Moreover, with this type of packaging, some undesirable small defects or scratches can appear on the outer surface of the syringe bodies due to repeated frictions of the syringe bodies against the chimneys, generated by the vibrations during their transportation. These defects or scratches are undesirable not only for aesthetic issues but also because their emergence is synonymous with generation of particles inside the tub, leading to the contamination of the syringes. In some cases, breakage of the syringes may even occur.

The main purpose of this invention is to overcome this drawback.

In parallel, the applicant has developed a new tray or nest wherein syringes with non-circular flanges are oriented, that is to say, where the flanges of the syringes are maintained in a predetermined position with a specific angle in the chimneys, and wherein the row of flanges can interlock with each other. This tray leads to a higher density of the syringe bodies in a standard tub, and therefore allows an increase of the number of syringes that can be transported in this tub.

But even with such packaging, the contact of the flanges with the upper ends of the chimneys is not avoided and therefore defects, scratches, breakage but also particles can be generated during the transportation of the syringe bodies in the tubs specially when the tubs are upside down.

The purpose of this invention is also to overcome this problem.

The packaging concerned comprises, in a way known per se, a tub sealable by a cover and containing a nest for supporting containers having each a flange.

According to the invention, the packaging also comprises a plate having a first side and a second side, said plate placeable proximate the flanges of the containers before sealing the tub; said plate comprising a first surface defined on said first side and intended to be placed in contact with the flanges and a second surface defined on said second side, said first surface being spaced apart from said second surface such that when said container is supported by the nest in the tub and said plate is located proximate the flange, the first surface contacts the flange, and said second surface is proximate the sealing cover.

The applicant has found that the problem of particles, scratches, or breakage should be induced by the movement of the containers, particularly syringes, in the holes and/or chimneys of the tray due to the clear space between the flanges and the sealing cover. Therefore, in order to avoid such movements or at least to reduce them, the applicant developed a plate according to the invention, which is in direct contact with the flanges of the syringes and the sealing cover.

The applicant has also found that the problem of the significant level of undesired scratches, particles, or even breakage can also occur when using trays or nests with oriented flanges. Indeed, with such trays or nests, the flanges can move with respect to the projections present on the trays or nests, provided for placing the flanges in the determined angular position. This move of the syringes leads to a loss of the determined orientation and can thus induce contacts between the different flanges, especially with this kind of trays or nests because the flanges are in the immediate vicinity one with each other, with imbrications.

The removal of the axial movement of the syringes obtained with the plate according to the invention allows to maintain the flanges in engagement with said projections and thus to maintain the flanges in their determined orientation when the tub is upside down, allowing therefore to overcome the aforementioned drawbacks.

The plate could comprise a single said first surface and a single said second surface; however, preferably, this plate has an profile with undulations forming ribs, these ribs forming said first surfaces, that is to say comprises a plurality of said first surfaces, each located in front of a row of syringe bodies, and a plurality of said second surfaces located on the side of the sealing cover.

Thus, this cover plate with undulations or slots contains less material than a plane-parallel cover plate and is particularly lighter and less expensive to manufacture, and can additionally be manufactured by thermoforming. Moreover, this kind of cover plate has the advantage of having a flexible structure, that allows it to be removed by winding, together with the sealing cover.

When the plate is removed by winding simultaneously with the withdrawal of the sealing cover, the plate needs to be made of flexible material suitable to be wrapped, or needs to have a non-stiffened structure in one direction, suitable to be rolled along this direction.

If the plate is removed by gripping and/or by aspiration, for example by means of suction cups, then the plate comprises at least one stiffening wall or a plurality of such stiffening walls.

The plate can also comprise at least one stiffening rib or a plurality of such stiffening ribs, for example stiffening ribs arranged in a way that, when being placed in the packaging, they are aligned with the rows of the syringe on the nest.

The plate can also comprise a continuous peripheral edge.

The plate can also comprise at least one full partition groove or a plurality of such full partition grooves.

The features above provide, individually or in combination, a rigidity to the cover plate allowing it to be removed by gripping and/or by aspiration.

The invention will be better understood and other characteristics and advantages thereof will become evident, with reference to the attached schematic drawings, representing, by way of non-limiting and not exhaustive examples, a preferred embodiment of the packaging, and several embodiments of a plate that comprises the packaging.

Figure 1:
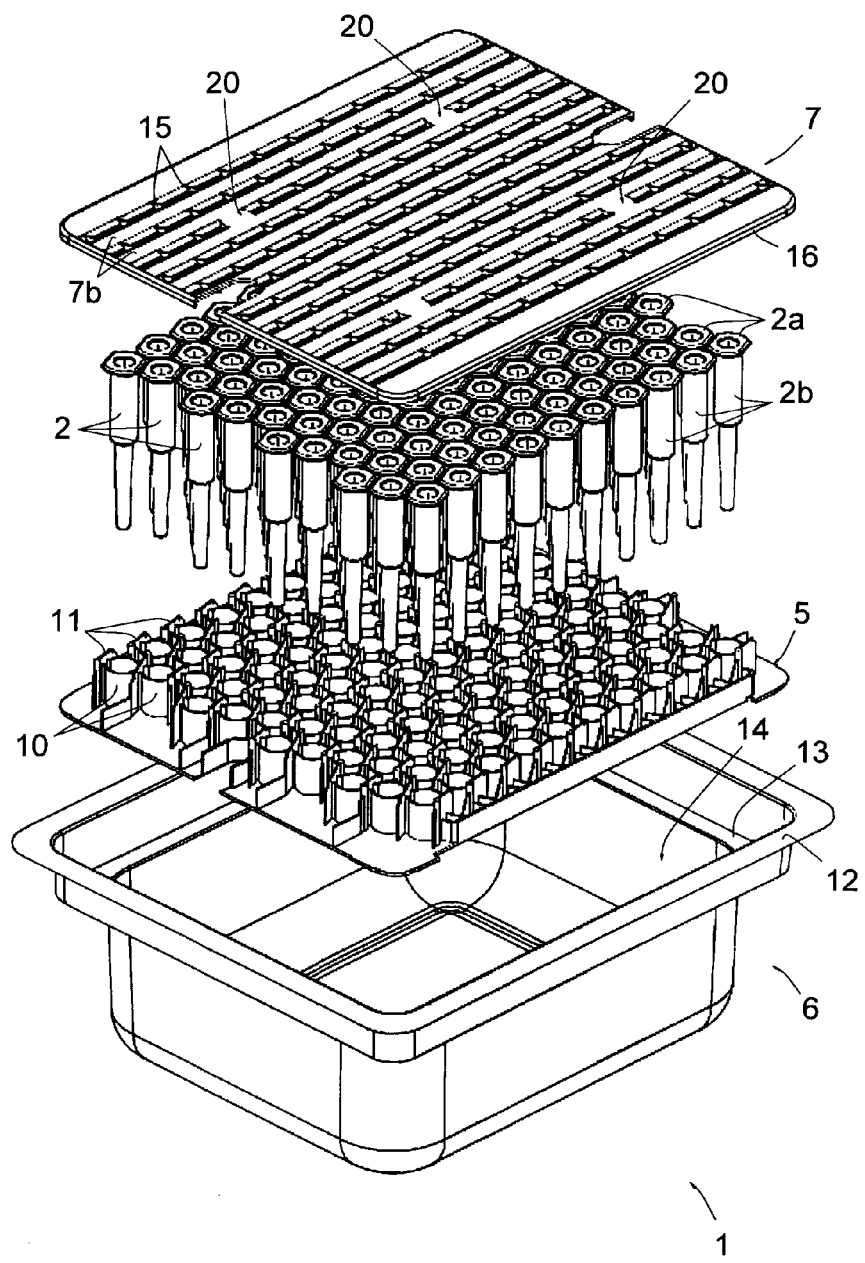
FIG. 1 is an exploded perspective view of the packaging, with a plate according to a first embodiment of the present invention.
Figure 2:
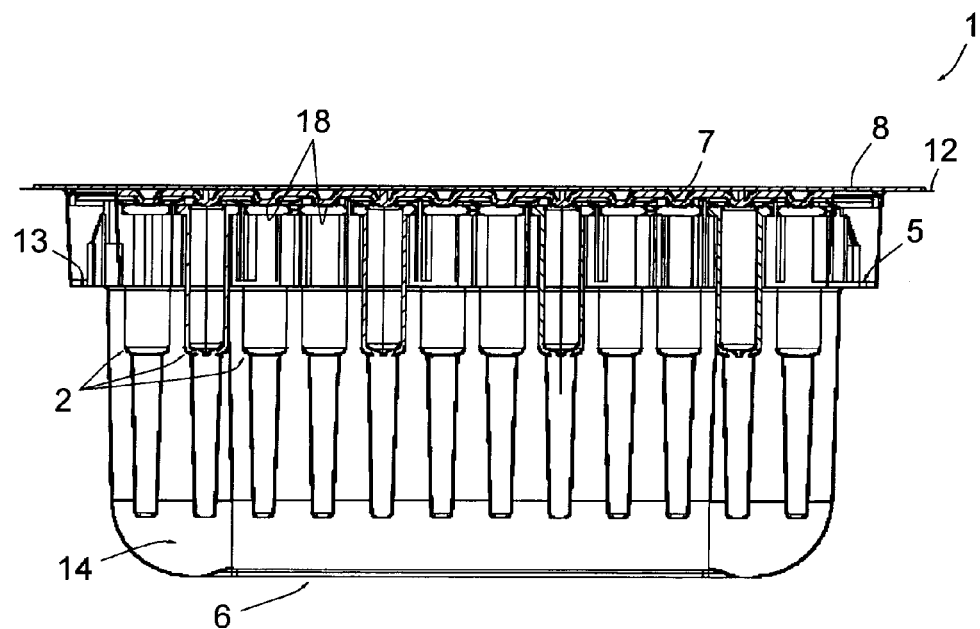
FIG. 2 is a cross section side view of a second embodiment, after sealing.
Figure 3:
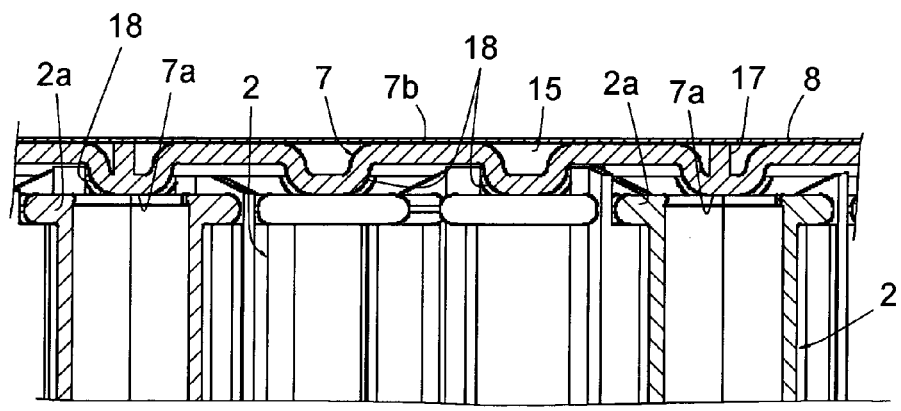
FIG. 3 is a view similar to FIG. 2, in an enlarged scale.

FIGS. 1 to 3 show a packaging 1 for the transport of syringes 2 from one site to another, comprising a grouping nest 5 for receiving the syringes 2, a tub 6, a plate 7 and a sealing cover 8 of this tub 6 (visible in FIGS. 2 and 3).

The grouping nest 5 comprises a plurality of openings coaxially surrounded by circular contiguous chimneys 10, and positioning projections 11 arranged between these chimneys 10. The circular chimneys 10 form adjusted housings for the cylindrical reservoirs of the syringes 2 and receive the proximal non-circular flanges 2a of the syringes 2 thereon when the cylindrical reservoirs or barrels 2b of the syringes 2 are fully engaged in these chimneys 10. The flanges 2a are inserted between the projections 11 in the position of complete engagement, in such a way that the projections 11 provide an angular direction of these flanges 2a so that the latter may be arranged near each other without contact with one another. Such arrangement is disclosed in the document of the patent application No PCT/IB2009/006907 of the same applicant.

The tub 6 has an upper flange 12 for sealing the sealing cover 8, an upper shoulder 13 for receiving the nest 5, and a bottom part 14 for housing the syringes 2 when the nest 5 is supported against the shoulder 13. The plate 7 is, like the nest 5 and the tub 6, made of a moulded synthetic material.

As shown more particularly in the embodiment described on FIGS. 2 and 3, the cover plate 7 can have an undulated profile seen in cross-section in FIG. 3. The distance between axes of the undulations corresponds to the distance between the rows of the syringes 2 on the nest 5, and the total thickness of the cover plate 7 corresponds to the distance separating the upper surface of the flanges 2a and the inner surface of the sealing cover 8, when the syringes 2 are placed on the nest 5 and the nest 5 is placed in the tub 6. As clearly shown in FIG. 3, the cover plate 7 thus defines a plurality of ribs 18 which form a plurality of first surfaces 7a intended to rest against the flanges 2a and a plurality of second surfaces 7b located on the side of the cover plate 7, on the opposite side of the first surfaces, the distance separating the first surfaces 7a and the second surfaces 7b being chosen in order to the first surfaces 7a rest against the flanges 2a when the second surfaces are in contact with the sealing cover 8.

In this embodiment, the cover plate 7 also comprises, on its surface forming the said second surfaces 7b, stiffening walls 15, and a continuous peripheral edge 16, extending over the side of the cover plate 7 on the opposite side of the surfaces 7b. The walls 15 are located in the cavities 21 formed on the upper side of the cover plate 7 by the ribs 18 that form the said first surfaces 7a, and are regularly arranged along these cavities 21, in order to be arranged transversally to said first surfaces 7a.

Due to this kind of structure, the cover plate 7 has a relatively high rigidity and can be removed by gripping and/or by aspiration, for example by means of suction cups.

As shown in FIG. 1, the cover plate 7 can also comprise bridges 20 (four are present on FIG. 1), i.e. areas without any cavities 21. These bridges 20 are placed in order to facilitate the removal of the cover plate 7 when suctions cups are used.

In an alternative embodiment, as shown on FIGS. 2 and 3, the cover plate 7 may also comprise stiffening ribs 17 perpendicular to the ribs 18, projecting from the bottom wall of these ribs 18. These stiffening ribs 17 connect adjacent walls 15 to improve the stiffness of the bottom side of the cover plate 7.

The sealing cover 8 is formed by a sheet of suitable heat sealable material, in particular by a sheet in Tyvek® (material sold by Dupont De Nemours Company).

With this plate 7 any axial movements of the syringes 2 in the chimneys 10 is avoided thanks to its simultaneous contacts with the flanges 2a and the sealing cover 8. In the absence of this cover plate 7, these movements would be possible due to the distance existing between the flanges 2a and the said sealing cover 8. This cover plate 7 thereby provides elimination of the problem of generation of marks, particles, scratches or breakage of the syringes 2 resulting from this possible axial movement.

The cover plate 7 also provides secured holding of the flanges 2a in engagement with the positioning projections 11 even in case of holding the package 1 upside down. It thus solves the problem of high level of undesired marks, particles and risk of breakage existing with a nest 5 on which the flanges 2a are maintained in a predetermined orientation by such projections 11.

Figure 4:
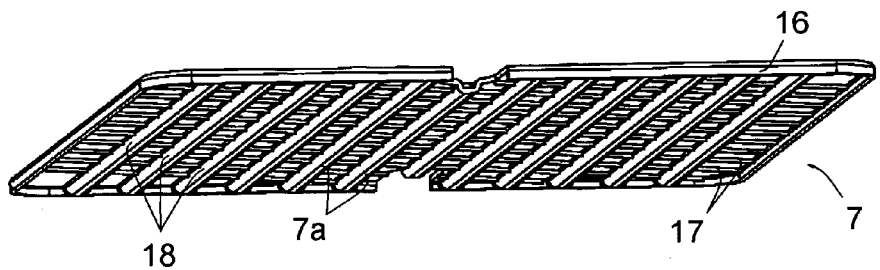
FIGS. 4 and 5 are perspective views, respectively bottom view and top view, of the plate according to another embodiment of the present invention.
Figure 5:
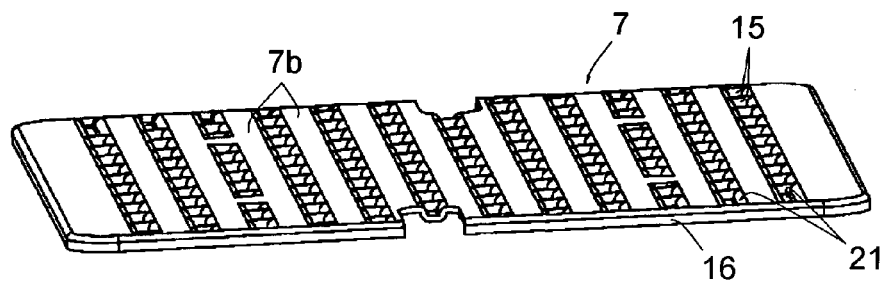

FIGS. 4 (bottom view) and 5 (top view) show another embodiment of the cover plate 7, which is intended to be removed by gripping and/or by aspiration. In this embodiment, the cover plate 7 is a rigid cover plate that can be made in moulded plastic. With respect to the embodiments of FIGS. 1-3, some walls 15 are located in the cavities 21 to reinforce the rigidity of the of the cover plate 7, and a continuous peripheral edge 16 is also present to clip the cover plate 7 on the tub 6.

Figure 6:
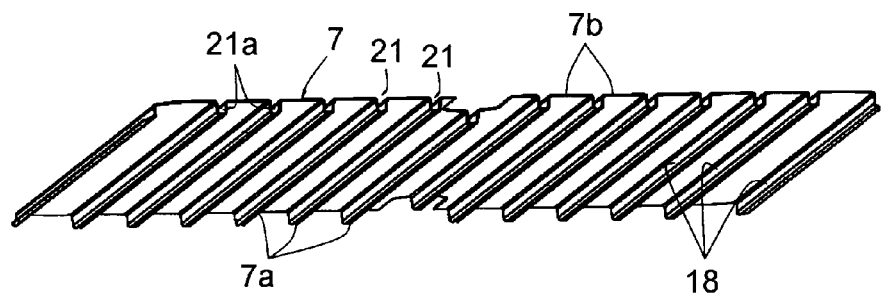
FIGS. 6 and 7 are perspective views, respectively bottom view and top view, of the plate according to another embodiment of the present invention.
Figure 7:
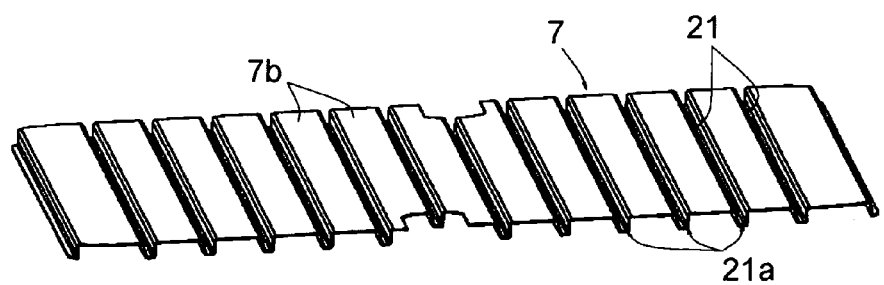

FIGS. 6 (bottom view) and 7 (top view) show yet another embodiment of the cover plate 7, wherein this cover plate is flexible and can be made by thermoforming. On these Figures, the cover plate comprises ribs 18 forming said first surfaces 7a extending on the whole transverse direction of the cover plate 7, and thus having full partition grooves 21 on the face opposed to the one on which the ribs 18 protrudes. These full partition grooves 21 rigidify the cover plate 7 in one main direction of the plate and lean on the flanges of the syringes. They can have outlets 21a on one side or on both sides of the cover plate 7.

This embodiment does not comprise any continuous peripheral edge 16. The outlets 21a, as well as the peripheral edge 16, allow the cover plate 7 to be clipped on the nest 5 when the syringes are placed on the nest. This cover plate 7 is intended to be removed by winding, simultaneously with the withdrawing of the sealing cover 8, and is adapted to be wrapped in a perpendicular direction to the ribs 18 or the full partition grooves 21.

As it has become evident from the foregoing, the invention provides a packaging for cylindrical containers, in particular for syringes, having, with respect to the packaging of the prior art, the determining advantages mentioned above.

The invention has been described above with reference to embodiments given by way of an example. Obviously, it is not limited to these embodiments and extends to all other embodiments covered by the appended claims.

The invention claimed is:

1. A packaging for cylindrical containers, the cylindrical containers each having a flange, said packaging comprising a tub sealable by a sealing cover and containing a nest for supporting the containers; a plate having a first side and a second side, said plate placeable proximate the flanges of the containers before sealing the tub; said plate comprising a plurality of first surfaces defined on said first side and intended to be placed in contact with the flanges and a plurality of second surface defined on said second side, said plurality of first surfaces being spaced apart from said-plurality of second surfaces such that when is the containers are supported by the nest in the tub the tub is sealed by the sealing cover and said plate is located proximate to the flanges, the plurality of first surfaces contacts the flanges, and said plurality of second surfaces contact the sealing cover, wherein the total thickness of the plate corresponds to a distance separating an upper surface of the flanges and an inner surface of the sealing cover when the containers are placed in the nest and the nest is placed in the tub such that the plate prevents axial movement of the containers with respect to the nest.

2. A packaging according to claim 1, wherein said plate has a profile with undulations forming ribs, these ribs forming said plurality of first surfaces.

3. A packaging according to claim 1, wherein said plate is made of flexible material.

4. A packaging according to claim 1, wherein said plate is flexible along at least one axis and is capable of being rolled along said at least one axis.

5. A packaging according to claim 1, wherein said plate comprises at least one stiffening wall.

6. A packaging according to claim 1, wherein said plate comprises at least one stiffening rib.

7. A packaging according to claim 6, wherein said plate has stiffening ribs so arranged that when being placed in the packaging, they are aligned with the containers supported by the nest.

8. A packaging according to claim 1, wherein the plate comprises at least one continuous peripheral edge.

9. A packaging according to claim 1, wherein the plate comprises at least one full partition groove.

10. A packaging according to claim 1, wherein said plate comprises a plurality of stiffening walls.

11. A packaging according to claim 1, wherein said plate comprises a plurality of stiffening ribs.

12. A packaging according to claim 1, wherein the plate comprises a plurality of full partition grooves.

\* \* \* \* \*

UNITED STATES PATENT AND TRADEMARK OFFICE
CERTIFICATE OF CORRECTION

Page 1 of 1

PATENT NO.      : 8,939,288 B2
APPLICATION NO. : 13/823417
DATED           : January 27, 2015
INVENTOR(S)     : Samuel Gagnieux et al.

It is certified that error appears in the above-identified patent and that said Letters Patent is hereby corrected as shown below:

In the Claims

Column 5, Line 7, Claim 1, delete "surface" and insert -- surfaces --

Column 5, Lines 8-9, Claim 1, delete "said-plurality" and insert -- said plurality --

Column 5, Line 9, Claim 1, delete "is the" and insert -- the --

Column 5, Line 10, Claim 1, delete "the tub the tub" and insert -- the tub, the tub --

Signed and Sealed this
Twenty-ninth Day of September, 2015

Michelle K. Lee
*Director of the United States Patent and Trademark Office*